(12) United States Patent
Nakahara et al.

(10) Patent No.: US 6,469,202 B2
(45) Date of Patent: Oct. 22, 2002

(54) METHOD FOR DISPOSAL OF SOLID CATALYST

(75) Inventors: Sei Nakahara, Hyogo (JP); Takeshi Nishimura, Hyogo (JP); Masahiro Motofuji, Hyogo (JP); Masatoshi Ueoka, Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/732,563

(22) Filed: Dec. 8, 2000

(65) Prior Publication Data

US 2001/0006930 A1 Jul. 5, 2001

(30) Foreign Application Priority Data

Dec. 15, 1999 (JP) .......................................... 11-356419

(51) Int. Cl.[7] .......................... C07C 69/52; C07C 67/48; B01J 38/00
(52) U.S. Cl. ........................ 560/205; 560/218; 502/20
(58) Field of Search ............................ 502/20; 560/205, 560/218

(56) References Cited

U.S. PATENT DOCUMENTS 5,124,291 A * 6/1992 Bremer et al. ................ 502/21

OTHER PUBLICATIONS

Kirk–Othmer Encyclopedia of Chemical Technology. Monograph: "Waste Treatment, Hazardous Waste" John Wiley and Sons (1998).*

* cited by examiner

Primary Examiner—Mukund J. Shah
Assistant Examiner—Zachary C. Tucker
(74) Attorney, Agent, or Firm—Mathews, Collins, Shepherd & McKay, P.A.

(57) ABSTRACT

A method for washing a spent solid catalyst is disclosed which is characterized by washing the solid catalyst used for the reaction of generating an esterified compound in a device packed with the solid catalyst, distilling the cleaning fluid in a distilling part, and circulating the fraction obtained by the distillation to an esterification reactor. According to this invention, the existing apparatus used during the process for the production of an esterified compound can be adopted without any modification, the water by-produced in the reaction for production an esterified compound and an alcohol as the raw material for esterification can be used as the cleaning fluid, and these effective components can be recovered from the cleaning fluid. Thus, the stimulation from the offensive odor and the volatile component which has heretofore posed a problem during the removal of the solid catalyst is eliminated and the safety in terms of heath and in terms of operation is secured.

9 Claims, 3 Drawing Sheets

METHOD FOR DISPOSAL OF SOLID CATALYST

BACKGROUND OF THE INVENTION

1. Field of the Invention

This invention relates to a method for the disposal of a spent solid catalyst impregnated with an organic substance. More particularly, this invention relates to a method for the disposal of a solid catalyst, e.g. a spent ion-exchange resin, which comprises causing the solid catalyst for use in an apparatus for the production of an esterified compound to be washed as contained within the apparatus before it is discarded.

2. Description of the Related Art

The esterified compound is generally a compound produced by the reaction of an alcohol with a carboxylic acid. The (meth)acrylic ester, for example, which is a raw material for commercial production is produced in a large scale plant comprising a step for producing (meth)acrylic acid by the reaction of catalytic gas phase oxidation, a step for purifying the (meth)acrylic acid, and a step for esterifying the (meth) acrylic acid with an alcohol.

At the step for the reaction of esterification, the reactor for forming an esterified compound is generally packed with a solid catalyst such as an ion-exchange resin for catalyzing the reaction. The solid catalyst tends to be deteriorated by continuation of the reaction. When this solid catalyst has the activity thereof degraded to a certain level, it becomes necessary to withdraw the exhausted solid catalyst from the esterified compound forming reactor and replace it with a newly supplied solid catalyst. At present, it is customary for this withdrawal to be carried out by human power.

Since the amount of the catalyst in the esterified compound forming reactor is large and since the catalyst is contained in an impregnated state in the reaction solution, the effect of the reaction solution, for example, on the health of a worker engaging in the withdrawal has come to pose a problem.

Figure 1:
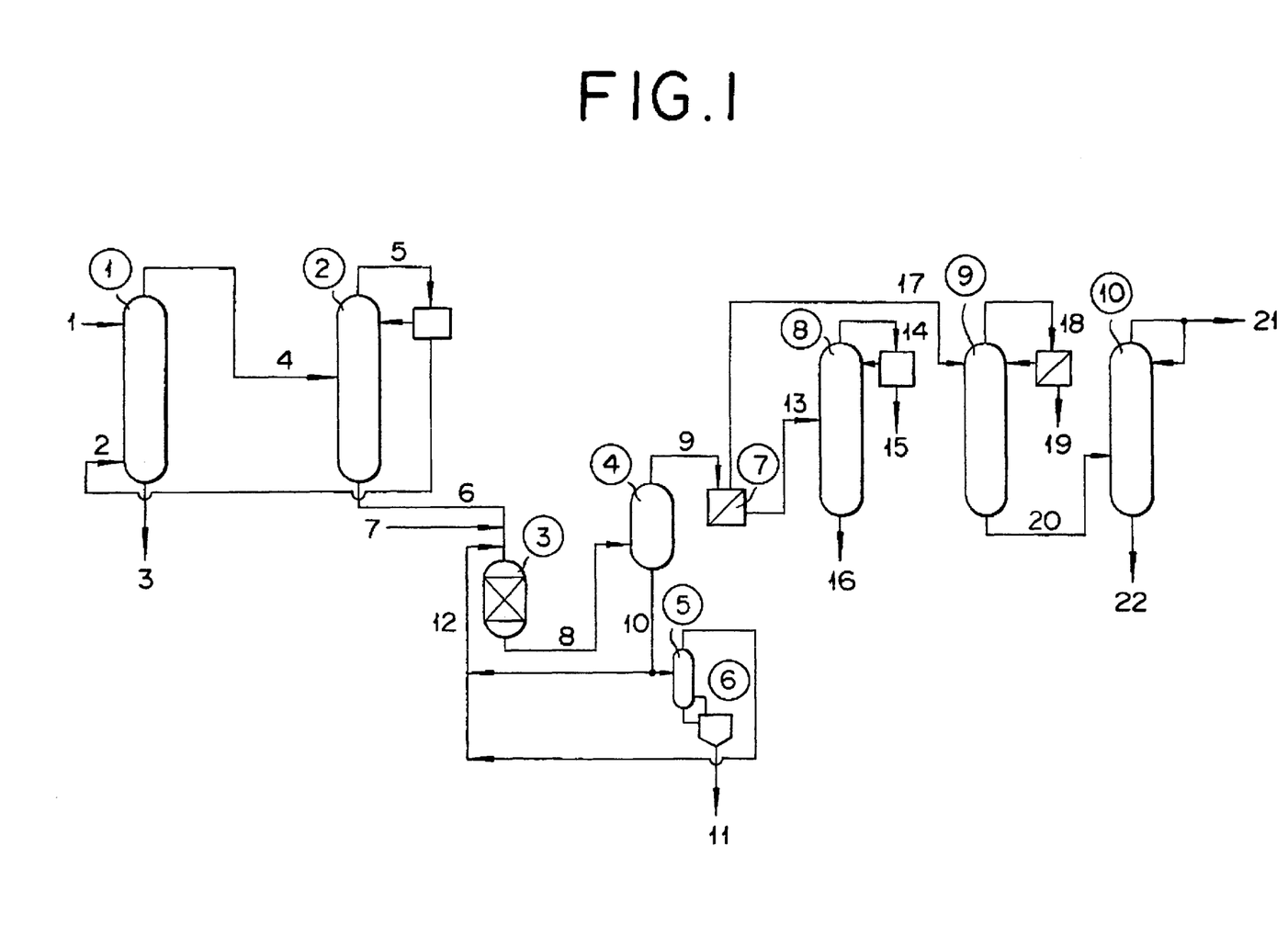
FIG. 1 is a schematic diagram illustrating the process for production of an esterified compound.

This step for the production of an esterified compound will be specifically described below with reference to FIG. 1 which illustrates one example of the production of a (meth)acrylic ester by a procedure comprising a step of producing (meth)acrylic acid through the reaction of catalytic gas phase oxidation and a subsequent step of esterifying this acid. With reference to FIG. 1, ① stands for a (meth)acrylic acid extraction column, ② for a solvent separation column, ③ for an esterification reactor, ④ for a vaporizer, ⑤ for a distillation column, ⑥ for a thin-film vaporizer, ⑦ for an oil-water separator, At for an alcohol stripper, ⑨ for a light boiling substance separation column, ⑩ for a high boiling substance separation column, 1 for an aqueous (meth)acrylic acid solution supply line, 2 for an extraction solvent supply line, 3 for a water phase emission line, 4 for a solvent phase supply line, 5 for a solvent fraction line, 6 for a crude (meth)acrylic acid supply line, 7 for an alcohol supply line, 8 for an esterification product supply line, 9 for a distilled fraction line, 10 for a high boiling substance supply line, 11 for a high boiling impurity extraction line, 12 for a recovered (meth)acrylic acid supply line, 13 for an alcohol-containing water phase supply line, 14 for a light boiling fraction line, 15 for a recovered alcohol extraction line, 16 for a waste water extraction line, 17 for a (meth)acrylic ester-containing oil phase supply line, 18 for a light boiling fraction line, 19 for an alcohol-containing water phase extraction line, 20 for a (meth)acrylic ester supply line, 21 for a (meth)acrylic ester product extraction line, and 22 for a high boiling substance extraction line.

First, the (meth)acrylic acid which is one of the raw materials for the production of an esterified compound is produced by the catalytic gas phase oxidation of propylene, acrolein, propane, isobutylene, methacrolein, etc. This reaction forms low boiling substances such as aldehyde, high boiling carboxylic acids such as terephthalic acid and benzoic acid, and such by-products of comparatively high boiling points as tarry substances besides the (meth)acrylic acid which is aimed at by the reaction. Thus, the gas containing the (meth)acrylic acid is sequestered with an absorbent such as water in an acrylic acid absorbing column (not shown) to obtain an aqueous (meth)acrylic acid solution and subsequently the aqueous (meth)acrylic acid solution is supplied via the line 1 to the (meth)acrylic acid extraction column ①. In the (meth)acrylic acid extraction column ①, the extraction solvent supplied through the line 2 and the aqueous (meth)acrylic acid solution are brought into counterflow contact with each other to induce extraction of the (meth)acrylic acid into a solvent phase. Then, the solvent phase containing the (meth)acrylic acid is supplied through the line 4 to the solvent separation column ② and the crude (meth)acrylic acid is extracted through the bottom of the solvent separation column ② and supplied through the line 6 to the esterification reactor ③.

The esterification reactor ③ is filled with a strongly acidic cation exchange resin as a solid catalyst and is utilized for causing the (meth)acrylic acid supplied through the line 6 and the alcohol supplied through the line 7 to undergo a reaction for forming an esterified compound through the medium of the catalyst. The esterification reactor ③, therefore, is destined to contain the (meth)acrylic acid and the alcohol as the raw materials for the production of the esterified compound, the (meth)acrylic ester and water as the products of reaction, and the solid catalyst. During the normal operation of the apparatus, therefore, for the purpose of separating the (meth)acrylic acid, etc. contained in the esterification reactor ③, the reaction solution is supplied through the line 8 to the vaporizer ④ the distilled therein and the (meth)acrylic ester, alcohol, and water are expelled by distillation through the top of the vaporizer ④ and they are supplied through the line 9 to the oil-water separator ⑦. The oil phase containing the (meth)acrylic ester separated in the oil-water separator ⑦ is supplied through the line 17 to the light boiling substance separation column ⑨ and distilled therein and the (meth)acrylic ester is extracted through the bottom of the light boiling substance separation column ⑨ and supplied through the line 20 to the high boiling substance separation column ⑩. In this separation column ⑩, the (meth)acrylic ester is rectified and the (meth)acrylic ester as a finished product is obtained through the line 21. Incidentally, the water phase which has been separated in the oil-water separator ⑦ is supplied, for the purpose of recovering the alcohol contained therein, to the alcohol stripper ⑧ and the alcohol is expelled by distillation through the top of the stripper and recovered from the line 15.

When the solid catalyst which is packed in the esterification reactor ③ is deteriorated by use and is discarded as mentioned above, it has been customary to effect the extraction of the deteriorated solid catalyst from the reactor by human power. The chemical stimulation from the raw materials for reaction, the product of the reaction, and the by-products and the physical obstruction such as adhesion of polymer compel the operator engaging in the work of discarding the spent solid catalyst to experience spiritual displeasure and arouse anxiety about possible infliction of an adverse effect on the operator's health. Further, in terms of safety, the solvent contained in the reaction solution entails the problem of threatening ignition. The disposal of the spent solid catalyst by human power is generally difficult, with the largeness of the volume of the esterification reactor ③ itself as a contributory factor.

More often than not, an ion-exchange resin is used as the solid catalyst which fills the esterification reactor ③, a main component of the apparatus for the production of the esterified compound, no matter whether the solid catalyst is used in a fixed-bed pattern or in a fluidized-bed pattern. The ion-exchange resin is a catalyst easy to deteriorate and, therefore, the esterification reactor ③ using this ion-exchange resin frequently needs to undergo an operation of disposal. In a large scale plant, however, the stop and the start of an operation require enormous labor and time and even partial stop of a component device necessitates adjustment of a series of relevant reaction conditions. When the stop of the esterification reactor results in degrading the productivity of the esterified compound aimed at by the operation, the object of attaining quantity production is crushed. Since the spent solid catalyst must be, therefore, discarded and replaced with a new supply quickly, the desirability of adopting the most efficient method for the disposal has been finding growing recognition. The term "fixed-bed pattern" refers to a method for performing a given reaction in an esterification reactor packed with a solid catalyst such as a strongly acidic cation-exchange resin in a fixed pattern and the term "fluidized-bed pattern" refers to a method for effecting a reaction of esterification by suspending and dispersing a solid catalyst like the fashion of the so-called fluidized bed, i.e. introducing a gas either with a stirring device or through the bottom part of an esterification reactor make an ion-exchange resin suspend and disperse in a reaction solution and the water formed by the reaction of esterification in the reaction solution is expelled by azeotropic distillation. The reaction solution which contains the ion-exchange resin is treated with a catalyst separation device such as a filter to effect separation of the ion-exchange resin and the reaction solution.

When the esterified compound happens to use such a reacting monomer as (meth)acrylic acid as one of the raw materials for the production thereof, the polymer of (meth) acrylic acid, the polymer of a (meth)acrylic ester, etc. possibly adhere to or accumulate on the solid catalyst to be discarded. The removal of these polymers which also adhere to the esterification reactor necessitates use of a washing solvent in a large volume. When the cleaning fluid thus used for the removal is discarded or disposed of as by combustion, the disposal entails generation of carbon dioxide and pollution of rivers and coasts with an organic solvent and results in violating environmental protection. Thus, the desirability of developing a means which is capable of disposing of the spent cleaning fluid with due consideration to the environmental protection has been finding public approval.

SUMMARY OF THE INVENTION

The present inventor, after studying in detail the process for the production of an esterified compound, has discovered that when water or a specific solvent is added to the esterification reactor and used therein for washing a spent solid catalyst contained in the reactor, an operator engaging in the work of extracting the solid catalyst from the esterification reactor is enabled to avoid experiencing displeasure and the useful substances contained in the cleaning fluid is enabled to be reused by using the cleaning fluid for distillation in a device operated in the apparatus for the production of the esterified compound. This invention has been perfected as a result. To be specific, the task imposed on this invention is accomplished by the following Item (1).

(1) A method for the disposal of a spent solid catalyst in an apparatus for the production of an esterified compound comprising an esterification reactor provided with a part packed with a solid catalyst and a distillation part, which method is characterized by washing the spent solid catalyst in the part packed with the solid catalyst with water and/or a component of the raw material for an esterifid substance.

According to this invention, the existing apparatus to be used in the process for production of an esterified compound can be operated in its unaltered form, the water by-produced in the reaction of esterification and the alcohol as a raw material for the esterification can be used as the cleaning fluid, and such effective components can be recovered from the cleaning fluid. Thus, the stimulation from the offensive odor and the volatile component which have heretofore posed a problem to the removal of the spent solid catalyst is eliminated and the safety in terms of health and in terms of operation is secured. Where a plurality of such esterification reactor are parallelly connected, the practice of discarding only the solid catalyst in part of these esterified compound generators brings the particular efficiency of enabling the disposal to be effected while retaining the existing working apparatus in continued operation.

DETAILED DESCRIPTION OF THE PREFERRED EMBODIMENTS

This invention concerns a method for the disposal of a spent solid catalyst in an apparatus for the production of an esterified compound comprising an esterification reactor provided with a part packed with a solid catalyst and a distillation part, which method is characterized by washing the spent solid catalyst in the part packed with the solid catalyst with water and/or a component of the raw material for an esterifid substance. When the spent solid catalyst is discarded without undergoing any washing and cleaning operation in advance, the varying components contained in the solid catalyst emit offensive odor and the volatile component of a certain kind possibly impairs the health of an operator engaging in the work of disposal. This danger is particularly prominent in a large-scale esterification reactor. This invention, by effecting recovery of the effective components contained in the cleaning fluid by using part of the apparatus being operated in the process for production of an esterified compound, enables the disposal of the spent solid catalyst to be carried out easily without requiring any special device, permits the operator engaging in the work of disposal to maintain health with due care, allows the operation to proceed safely, and confers an exalted improvement on the work environment. Now, this invention will be described specifically below.

The method for the disposal of a spent solid catalyst contemplated by this invention is intended for the apparatus for the production of an esterified compound which comprises an esterification reactor provided with a part packed with a solid catalyst and a distillation part. When the apparatus is equipped with such auxiliary components as mentioned above, it is at an advantage as pointed out above in enabling the effective components contained in the cleaning fluid which has given a wash to the spent solid catalyst to be easily washed and recovered by distillation without using any new special device. The apparatus to be used in this invention for the production of an esterified compound is required to be equipped at least with an esterification reactor provided with a part packed with a solid catalyst and a distillation part. It may be provided safely with an absorbing column and a rectifying column for the raw material of the esterified compound, a solvent extraction column, a rectifying column for the esterified compound, and a solvent separation column besides the auxiliary components mentioned above.

The term "distillation part" mentioned above refers to a device to be incorporated in the apparatus for the production of the esterified compound mentioned above. This device does not need to be particularly discriminated but is only required to be capable of performing an operation of heating a liquid and converting it provisionally into steam by utilizing the differences of the components in volatility and boiling point and then liquefying the steam thereby effecting refinement and separation. The object of the distillation of interest, therefore, may be the component of the raw material for the esterified compound, the reaction solvent, or the by-product, and may further embrace the case of not containing the word "distillation" in the designation. As concrete examples of the distillation part used in this sense, a distiller, a still, a thin-film vaporizer, a solvent separation column, an alcohol stripper, an azeotropic separation column, a light boiling separation column, and a high boiling separation column may be cited. Among them, the distillation part which is intended to perform fractional distillation of the component of the raw material for the esterified compound proves particularly advantageous. Despite the fact that this invention consists in a method for washing a solid catalyst, this distillation part is capable of using the recovered cleaning fluid and distilling it to recover the necessary component and putting the recovered component to re-use in the apparatus for the production of the esterified compound.

The reaction for the generation of an esterified compound in the apparatus for the production of an esterified compound is intended to mean a compound which has a structure such that this compound is formed from an organic acid and an alcohol with the elimination of water. It does not need to be limited to the case of actually forming an ester from an acid and an alcohol with the loss of water. Besides the case of obtaining an esterified substance (RCOOR') from a carboxyl group-containing compound (RCOOH) and a hydroxyl group-containing compound (R'OH), for example, the case of obtaining an esterified compound (R'COOR') by the reaction of transesterification of a carboxylic ester (R'COOR) and a hydroxyl group-containing compound (R'OH) is embraced. Further, the esterified compound contemplated by this invention further embraces such a reaction of addition esterification that obtains $RCOOCH_2CH_2OH$ from acrylic acid ($CH_2$=CHCOOH) or methacrylic acid ($CH_2$=C($CH_3$)COOH) and an alkylene oxide. This invention can be extensively applied to a wide range of cases using a solid catalyst in such reactions mentioned above.

The carboxyl group-containing compounds which are usable in the process for the production of the esterified compound are properly saturated or unsaturated carboxylic acids of 1–10 carbon atoms, preferably carboxylic acids of 2–4 carbon atoms. As concrete examples of the carboxyl group-containing compounds which can be advantageously used in this invention, acetic acid, acrylic acid, methacrylic acid, fumaric acid, maleic acid, and lactic acid may be cited.

The hydroxyl group-containing compounds are properly lower aliphatic alcohols or lower alicyclic alcohols. The reason for using such a hydroxyl group-containing compound is that it exhibits an excellent washing efficiency when it is used for cleaning a solid catalyst. As concrete examples of the hydroxyl group-containing compounds, various alcohols such as methanol, ethanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 1-ethylhexanol, isononyl alcohol, and lauryl alcohol may be cited. These alcohols may be in a linear form or in a branched form. These alcohols may be used either singly or in the form of a combination of two or more members. Since the hydroxyl group-containing compound which is contained in the cleaning fluid can be fractionated during the process of distillation, it can be eventually recovered effectively and put to use.

As concrete examples of the alkylene oxide, ethylene oxide, propylene oxide, butylene oxide, etc. may be cited.

The solid catalyst for use in this invention does not need to be particularly discriminated but is only required to be a solid catalyst which can be used in the reaction for the generation of an esterified compound. Generally, the strongly acidic cation-exchange resin which is widely used in the reaction for the generation of an esterified compound is properly used herein. Commercial products of strongly acidic cation-exchange resin which are available in the market are generally usable herein. As concrete examples of such commercial products, Amberlite 16 and Amberlite IR-120B (made by Rohm and Haas Company), Diaion PK-208, PK-228, and PK-216 (made by Mitsubishi Chemical Co.), Duolite C-26 and Duolite ES-26 (made by Sumitomo Chemical Co.), and MSC-1, 88 (made by Dow Chemical Co.) may be cited.

The expression "part packed with a solid catalyst" as used in this invention refers to the part which is located in the esterification reactor and packed a solid catalyst. When the esterification reactor is a fixed bed pattern, therefore, this expression refers to the interior of the esterification reactor which is packed with an ion-exchange resin. When the esterification reactor is a fluidized bed pattern, the expression refers to not only a vessel packed with the ion-exchange resin but also a separation vessel for separating the ion-exchange resin and a liquid reaction product. The reaction for the generation of an esterified compound is generally carried out in a liquid phase by using a device of the fluidized-bed pattern or the fixed-bed pattern at a temperature in the range of 50–110° C. When such an easily polymerizing substance as, for example, acrylic acid or methacrylic acid is used as the raw material for the reaction of esterification, it is optional to add a polymerization inhibitor to the relevant reaction solution. As concrete examples of the polymerization inhibitor which is usable herein, hydroquinone, methoxyhydroquinone, methylene blue, and phenothiazine may be cited.

This invention, when the solid catalyst used in the reaction for the production of the esterified compound is deteriorated or degraded in catalytic activity by the polymer by-produced during the reaction of esterification and is consequently required to be discarded, causes this spent solid catalyst to be washed with water and/or other cleaning fluid as retained in the part packed with the solid catalyst before it is discarded. The solid catalyst is generally contained as impregnated with the carboxyl group-containing compound and the hydroxyl group-containing compound as the components for the raw material and the ester as the product of reaction. It is, therefore, washed preparatorily with water or the components for the raw material for the esterified compound. The water to be used for the washing under discussion may be water of any sort such as, for example, one member selected from the group consisting of tap water, purified water, and industrial water. For this invention, however, it is commendable to use the water which is by-produced in the reaction for esterification. The use of this water herein constitutes itself effective utilization of waste water because the water by nature has been heretofore discarded for the sake of the promotion of the reaction for esterification.

This invention permits the components of the raw material for the esterified compound to give a wash to the solid catalyst together with or in addition to the water mentioned above or prior to the wash with the water. The components of the raw material for the esterified compound mentioned above include the hydroxyl group-containing compound, the carboxylic group-containing compound, the solvent, etc. which are used in the reaction for the production of the esterified compound. They are in a liquid state at normal room temperature and, therefore, are suitable for washing the spent solid catalyst and easily reusable as well. Thus, the cleaning fluid does not need to be discarded and suffered to bring an adverse effect on the environment and, consequently, is enabled to contribute to the effective utilization of natural source.

Properly the cleaning of the solid catalyst with water or the components of the raw material for the esterified compound is carried out as heated to a temperature in the range of 20–100° C., preferably 30–100° C., and particularly preferably 50–100° C. The heating is preferable because it is capable of effectively depriving the solid catalyst of the components of the raw material for the esterified compound, the by-product of the reaction, and the esterified compound which are deposited to the solid catalyst. Particularly when the cleaning fluid is an alcohol which is one of the components of the raw material for the esterified compound, the cleaning fluid consequently obtained can be used in its unaltered form in the esterification reactor (3 among other component devices of the apparatus for the production of the esterified substance. When the cleaning fluid is supplied to the alcohol stripper (8), the alcohol which is obtained as a distillate in the stripper (8) can be re-used for the reaction of esterification and, what is more, the water which is obtained as the bottoms of the stripper (8) can be utilized as the cleaning fluid. The solid catalyst, therefore, can be washed solely with the raw material for the esterified compound or the by-product of the relevant reaction and, particularly advantageously, the effective components contained in the cleaning fluid can be efficiently re-used.

Figure 2:
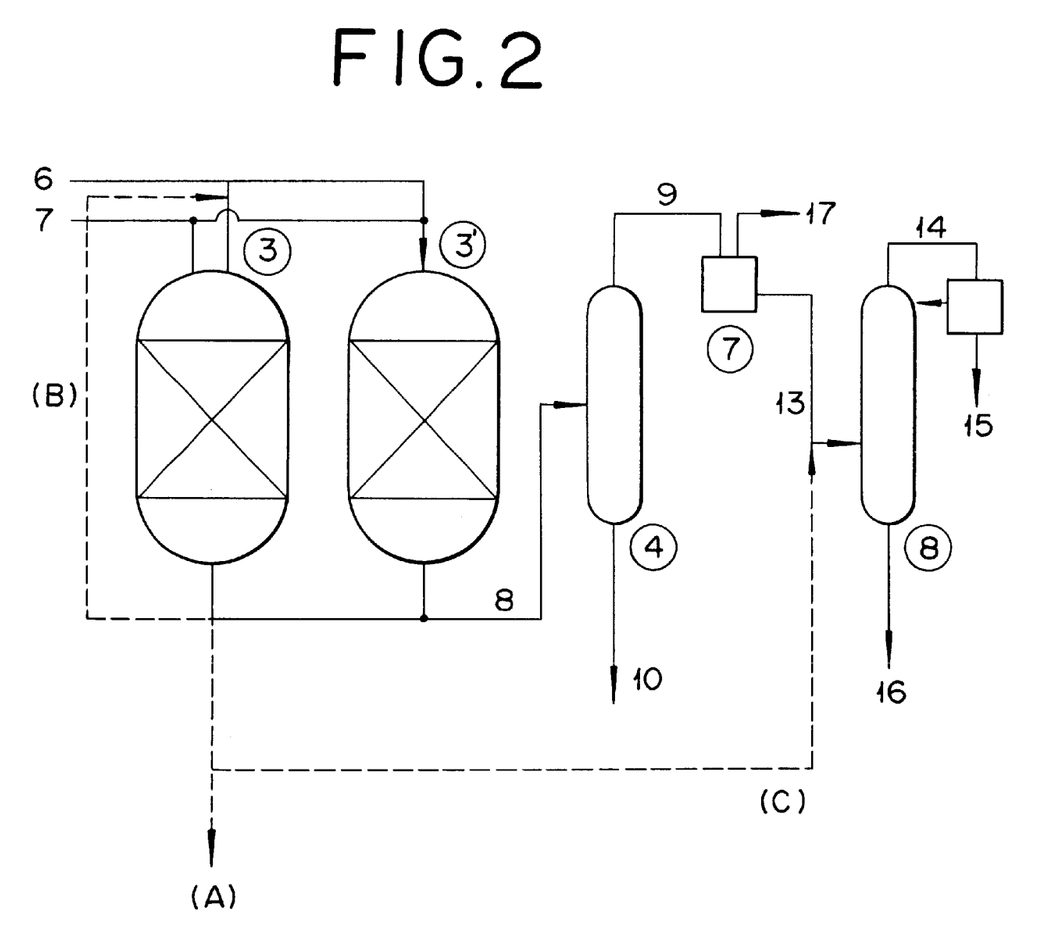
FIG. 2 is a schematic diagram illustrating the process for washing a solid catalyst in an esterification reactor of the fixed-bed pattern according to this invention.

Now, as a preferred mode of embodying this invention, a method for washing a spent solid catalyst in the esterification reactor (3) packed with the catalyst in the fixed-bed pattern in a process for the production of a methacrylic ester by the esterification of methacrylic acid obtained by the reaction of catalytic gas phase oxidation with an alcohol in a plurality of esterification reactor (3) and (3)' will be described with reference to FIG. 2. The reference numerals used in FIG. 2 are identical with those used in FIG. 1. The reference numeral (3)' denotes an esterification reactor.

The methacrylic acid as a raw material for the production of an esterified compound is obtained in a process for the reaction of catalytic gas phase oxidation of isobutylene, tertiary butanol, methacrolein, or isobutyl aldehyde. This methacrylic acid and an alcohol which is another component of the raw material for the relevant production are subjected to a reaction for the production of an esterified compound in the esterification reactor (3), (3)'. When the catalyst for the reaction is placed in the fixed-bed pattern in the esterification reactor, the components of the raw material mentioned above are caused to flow down the catalyst.

When the solid catalyst used in the esterification reactor (3) alone is deteriorated during the process for the production of the esterified compound as described above, the operation of the esterification reactor (3)) is stopped and the operation of the other auxiliary components of the apparatus is left continuing and the reaction solution in the esterification reactor (3) is withdrawn through the lower part of the reactor (3). This reaction solution is forwarded in its unaltered form to the vaporizer (4) and subjected to purification of the formed ester therein.

Then, with the spent solid catalyst left standing in the esterification reactor, the alcohol as one component of the raw material is introduced into the esterification reactor (3) during the normal course of the process for the production of the esterified compound and washed by being circulated through the line (B). The temperature of the alcohol used for washing, therefore, is only required to be at the temperature at which the alcohol is introduced into the esterification reactor (3). optionally, the alcohol may be heated in advance to the preferred temperature of the cleaning fluid mentioned above. The heating under discussion may be accomplished by using a temperature adjusting device for the reactor (3) as in the case of a normal operation. Incidentally, the amount of the alcohol to be introduced into the esterification reactor (3) does not need to be particularly restricted. The cleaning fluid which has been circulated is withdrawn through the line (A). Though the cleaning fluid mentioned above can be discarded from the process for disposal of a solid catalyst, it prefers to be re-used. The re-use may be made in the process for the production of the esterified compound or in other process of production. When the components contained in the cleaning fluid are reusable in the process for the production of the esterified compound, however, the re-use is attained easily in this process. The re-use in this manner is implemented by recovering the washed alcohol withdrawn through the line (A) as a raw material and transferring the recovered alcohol to the esterification reactor (3) in the process for the production of the esterified compound and putting it to re-use therein. The withdrawal through the line (A) does not need to be performed just once but may be performed a plurality of times or even continuously. The washing is preferred to be continued till the concentration of the esterified compound in the cleaning fluid is lowered fully satisfactorily.

Then, the water by-produced by the reaction of esterification and contained in the bottoms of the alcohol stripper (8) accumulated by the operation of the process for the production of the methacrylic ester is supplied to the esterification reactor (3) and washed therein in the same manner as the washing with an alcohol. No particular limitation is imposed on the amount of the water thus introduced into the esterification reactor (3). The washing is terminated at the time that the fall of the alcohol concentration in the cleaning fluid reaches a fully satisfactorily level. The cleaning fluid which contains the water occurring when washing with water is performed after the washing with an alcohol as described above may be distilled in the alcohol stripper ⑧ incorporated in the apparatus for the production of the esterified compound, with the result that the alcohol consequently recovered through the top of the stripper will be used in the esterification reactor ③. Thus, the cleaning fluid is introduced through the line (C) into the alcohol stripper ⑧ to permit recovery of the alcohol through the top of the stripper. In this case, the bottoms of the alcohol stripper ⑧ is circulated to the esterification reactor By and used as a cleaning fluid therein. Since the alcohol stripper ⑧ is generally operated under normal pressure, the procedure just described permits the solid catalyst in the esterification reactor to be efficiently washed by circulating to the esterification reactor ③ the cleaning fluid having a temperature in the neighborhood of 100° C. As the cleaning fluid, tap water or industrial water introduced from an external source may be used instead of the bottoms of the alcohol stripper ⑧. Particularly in the case of a reaction of addition esterification, no water is by-produced in the process for the production of an esterified compound. Even in this case, the present invention can be carried out.

Subsequently, after the necessary fall of the alcohol concentration in the cleaning fluid is confirmed, the supply of the cleaning fluid from the alcohol stripper ⑧ is stopped and the cleaning fluid is withdrawn from the esterification reactor ③. Then, the solid catalyst is to be extracted from the esterification reactor ③. Since the washed solid catalyst is free from the otherwise possible adhesion of the raw material for the esterified compound or the product of esterification, the operation of withdrawing the washed solid catalyst can be carried out without exposing the worker to the displeasure of offensive odor. When the final wash is given with water, it proceeds safely without entailing the danger of ignition with an organic solvent. When the esterification reactor ③, ③' are parallelly connected as illustrated in FIG. 2, the disposal by discarding can be effected without lowering the efficiency of production of the methacrylic ester as the target product because the operation of discarding the solid catalyst in the esterification reactor ③ can be carried out without interrupting the operation of the esterification reactor By When only one esterification reactor is in use as when the esterification reactor ③ is alone used, the washing described above is carried out, when necessary, after the device subsequent to the esterification reactor ③ is stopped. In this case, the cleaning fluids obtained in different runs of washing can be easily re-used when they are recovered and stored as sorted by origins. After the process for the production of the esterified compound has been operated, the cleaning fluids are supplied to the steps such as, for example, the vaporizer ④ and the alcohol stripper ⑧ which fit the components contained the cleaning fluids, with the result that the components will be recovered and put to re-use.

The description, as given above, has assumed use of an alcohol as the component of the raw material for the esterified compound. The solid catalyst can be washed by using a carboxylic group-containing compound in the same manner as described above. In this case, the cleaning fluid using the carboxylic group-containing compound can be supplied in its unaltered form to the esterification reactor ③ in the apparatus for the production of an esterified compound. Thereafter, the cleaning fluid resulting from the washing with water serves in the apparatus for the production and purification of the raw material for the esterified compound the purpose of recovering an acid contained in the cleaning fluid and allowing the recovered acid to be used in the esterification reactor ③. When the spent solid catalysts occurring in a plurality of esterification reactors are to be wholly discarded, the washing and the discarding can be carried out in the same manner as described above by stopping the relevant devices subsequent to the esterification reactors.

The method for washing, as described above, washes the solid catalyst first with the components of the raw material for the esterified compound and then with water. This order of washing is irrelevant; the solid catalyst may be washed first with water and then with the components of the raw material for the esterified compound and may be further washed with water. Optionally, a mixed liquid consisting of water and components of the raw material for the esterified compound may be used for the washing and cleaning under discussion. For the sake of removing the components of the raw material for the esterified compound, however, the washing at the final stage must be made with water.

The method of this invention for the disposal of a solid catalyst can be advantageously used in the process for the production of such esterified compounds as methyl acrylate, ethyl acrylate, butyl acrylate, isobutyl acrylate, 2-ethylhexyl acrylate, methyl methacrylate, ethyl methacrylate, butyl methacrylate, cyclohexyl methacrylate, 2-hydroxyethyl acrylate, hydroxy-propyl acrylate, 2-hydroxyethyl methacrylate, and hydroxypropyl methacrylate.

Figure 3:
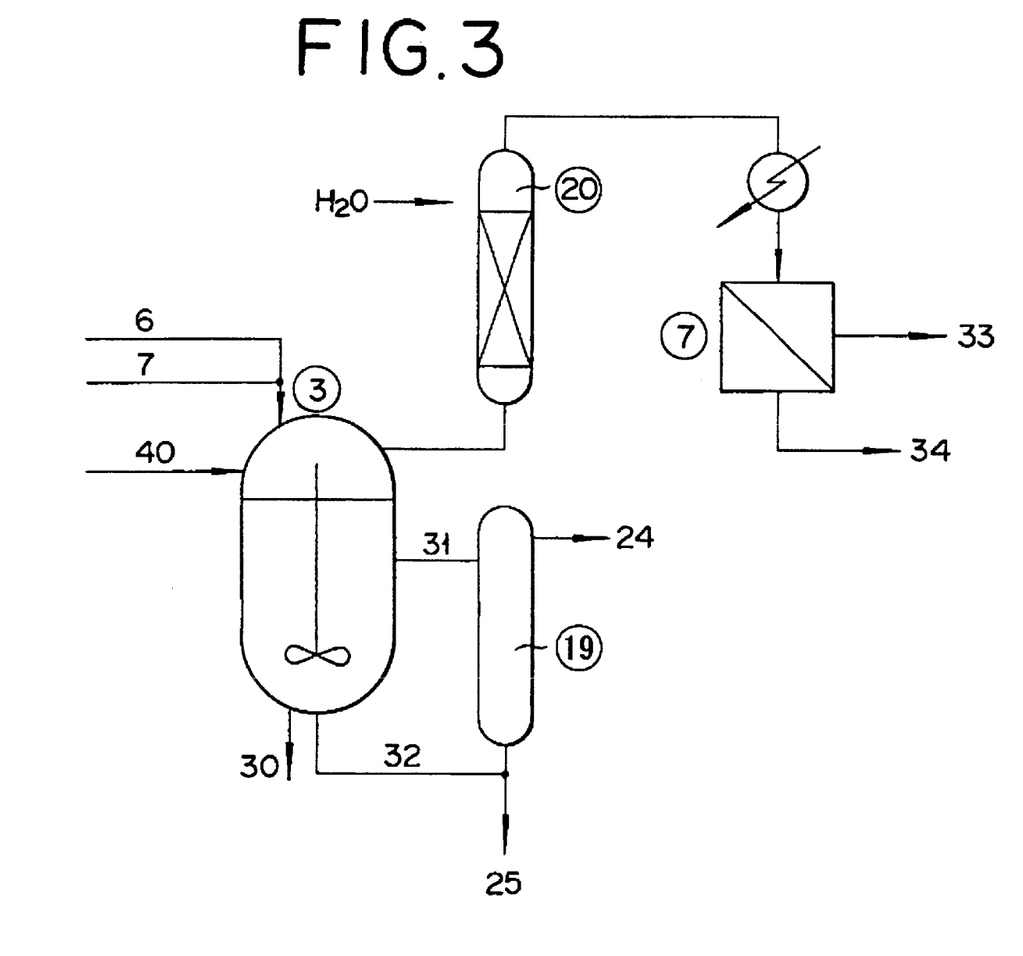
FIG. 3 is a schematic diagram illustrating the process for washing a solid catalyst in an esterification reactor of the fluidized-bed pattern according to this invention.

Now, the method for washing and cleaning a solid catalyst in the case of producing an acrylic ester by the use of the esterification reactor ③ of the fluidized-bed pattern will be described below with reference to FIG. 3. The reference numerals used in FIG. 3 are identical with those used in FIG. 1, excepting that 24 stands for a clarification fluid extraction line, 30 for a discharge line, 31 for a reaction solution extraction line, 32 for a resin circulation line, 33 for an azeotropic solvent extraction line, ⑳ for a dehydration column, and ⑲ for a resin separation vessel.

First, during the normal operation, the esterified compound is produced by supplying raw material compounds through the lines 6 and 7 to esterification reactor ③ which has been charged in advance with a solid catalyst. When the esterification by-produces water, the by-produced water may be subjected to azeotropy in the esterification reactor ③ with an azeotropic dehydrating solvent placed in advance in the esterification reactor ③. The reaction solution containing the esterified compound and the catalyst inside the esterification reactor ③ is introduced through the line 31 into the resin separation vessel ⑲ and left standing therein till precipitation of the solid catalyst. Then, the esterified compound no longer containing the solid catalyst is transferred through the clarification fluid extraction line 24 to the subsequent step. The precipitated solid catalyst is circulated together with part of the reaction solution to the esterification reactor ③. Incidentally, the azeotropic solvent and the by-produced water which are introduced into the dehydration column ⑳. Through the upper part of this column, the azeotropic solvent and the by-produced water are expelled by distillation and they are separated in the oil-water separator ⑦. The azeotropic solvent is discharged through the line and refluxed to the top of the dehydration column ⑳ and the water phase is discharged through the line 34. When the raw material alcohol is sparingly soluble in water and can be used as the azeotropic solvent for the by-produced water, the raw material alcohol may be used as the azeotropic solvent.

When it becomes necessary to discard the solid catalyst as when the solid catalyst has the performance thereof degraded to the point of exhaustion during the process for the production of an esterified compound as described above, the reaction solution is extracted through the line 30 after the esterification reactor ③ is stopped and the subsequent system is then stopped optionally. This reaction solution can be supplied to the process for the purification of an ester and purified therein. Then, the esterification reactor ③ is supplied with water through the line 40 or through the top of the dehydration column ⑳ and it is internally heated to expel by distillation the water together with the remaining alcohol component and ester component through the top of the distillation column ⑳ which continues to the esterification reactor ③. When the alcohol as the component of the raw material for the esterified compound is butanol or 2-ethylhexanol and is sparingly soluble in water as described above, the esterification reactor ③ and the water added thereto are heated together to expel by distillation the water, the alcohol, and the ester component and consequently recover the oil phase (alcohol phase and the ester component) through oil-water separation.

As concerns the water which is supplied through the line 40 or the top of the dehydration column ⑳, the water phase in the line 34 which has been separated by condensing the steam discharged through the top of the dehydration column ⑳ and introducing the resultant condensate to the oil-water separator ⑦. By using the devices operated in the process for the production of the esterified compound as described above, it is made possible to wash the solid catalyst easily, recover the components of the raw material contained by using them in the process, and put the recovered component to re-use.

Preferably, the interior of the esterification reactor ③ charged in advance with water is heated and the solid catalyst contained therein is stirred. This treatment is advantageous in respect that it permits efficient separation of the ester component and the alcohol component which adhere to the solid resin. Then, the solution in the esterification reactor ③ is introduced through the line 31 into the resin separation vessel ⑲ in the same manner as in the ordinary operation. In this case, it is preferred to omit the extraction through the line 24 of the resin separation vessel ⑲ annexed to the esterification reactor ③ and circulate the water containing the solid catalyst and emanating through the line 31 of the resin separation vessel ⑲ to the esterification reactor ③ through the line 32. This method is proper because it permits continuous supply of the water to the esterification reactor ③ so as to wash the solid resin and induce continuous introduction of the alcohol and the ester component contained therein into the dehydration column ⑳ and consequent continuous recovery of the alcohol and the ester component in the oil-water separator ⑦.

Incidentally, the alcohol which is expelled by distillation through the line 33 can be introduced as a raw material into the esterification reactor ③ and reused for the process for the production of the esterified compound. When the water phase through the line 34 contains a trace of alcohol, particularly butanol, it is permissible for the purpose of recovering the alcohol to transfer the water to an alcohol stripper (not shown) and distill it therein so as to recover the alcohol, add the bottoms (water) to the water phase through the line 34. Otherwise, the water may be supplied to the tops of the esterification reactor ③ and the dehydration column ⑳ and used as wasting water therein.

Incidentally, the end point of the washing is the time at which the concentration of the alcohol and the ester in the cleaning fluid is lowered fully satisfactorily. Subsequently, the heating is discontinued, the water is extracted from the esterification reactor ③, and then the solid catalyst is discharged. By this method of disposal, the solid catalyst present in the esterification reactor ③ and the solid catalyst present in the resin separation vessel ⑲ can be simultaneously washed.

Even in the fluidized-bed pattern described above, the solid catalyst can be washed with the component of the raw material for the esterified compound such as, for example, an alcohol before it is washed with water.

In this invention, the supply of the cleaning fluid to the rectification column and the alcohol stripper for the purpose of allowing re-use thereof in the apparatus for the production of the esterified compound may be implemented by a manual operation or by the use of a special line laid specifically for the sake of this supply. It is also permissible to store the cleaning fluid till a fixed volume and then put it to re-use.

EXAMPLES

Now, the present invention will be described more specifically below with reference to working examples.

Example 1

By the use of an apparatus adapted for the production of an esterified compound and provided with two fixed-bed type esterification reactors as illustrated in FIG. 2, a spent ion-exchange resin placed in a fixed-bed type esterification reactor ③ operated during the production of methyl methacrylate from methacrylic acid and methanol with a strongly acidic cation-exchange resin (made by Mitsubishi Chemical Co. and sold under the product code of "PK-208") as a catalyst was washed.

First, in an apparatus having parallelly connected the fixed-bed type esterification reactor ③ and esterification reactor ③' both having an inner volume of 10 m$^3$, the supply of the raw material to the esterification reactor ③ is stopped while the various devices connected to the esterification reactor ③' were kept in normal operation and the the reaction solution remaining in the esterification reactor ③ is extracted through the bottom part of the reactor ③. The extracted solution was supplied together with the reaction solution of the esterification reactor ③' through the line 8 to the vaporizer ④ and distilled therein.

Then, methanol was supplied through the alcohol supply line 7 to the esterification reactor ③ till the reactor ③ was filled to capacity, the ion-exchange resin was washed for one hour while the methanol was circulated by the use of the line (B), and the cleaning fluid was withdrawn through the line (A). The extracted cleaning fluid having methanol as a main component was supplied as a raw material alcohol to the esterification reactor ③'. After this procedure was performed up to two repetitions, water was supplied to the esterification reactor ③ till it was filled to capacity and the ion-exchange resin was washed for three hours while the water was circulated by the use of the line (B). Thereafter, the cleaning fluid was supplied through the line (C) at a flow rate of 1 m$^3$/h to the alcohol stripper ⑧, the ion-exchange resin was washed while the water heated to 100° C. was returned through the bottom of the alcohol stripper ⑧ to the esterification reactor ③ and, at the same time, the metanol in the cleaning fluid was recovered through the top of the alcohol stripper ⑧ and supplied as a raw material alcohol to the esterification reactor ③'. When this procedure was continued for 30 hours, the methanol concentration in the outlet solution from the esterification reactor ③ was found to have fallen to below 0.1 mass %. Thus, the supply of the bottoms of the alcohol stripper ⑧ was switched to that of water of normal room temperature, the esterification reactor ③ was cooled, the supply of water thereto was stopped, and the water was withdrawn therefrom. When the ion-exchange resin was subsequently withdrawn from the esterification reactor ③, it emitted practically no perceptible offensive odor.

Example 2

By the use of an apparatus adapted for the production of an esterified compound and provided with a fluidized-bed type esterification reactor as illustrated in FIG. 3, a spent ion-exchange resin placed in a fluidized-bed type esterification reactor ③ operated during the production of butyl acrylate from acrylic acid and n-butanol with a strongly acidic cation-exchange resin (made by Mitsubishi Chemical Co. and sold under the product code of "PK-208") as a catalyst was washed.

First, the supply of the raw material through the lines 6, 7 to the fluidized-bed type esterification reactor ③ having an inner volume of 10 m³ was stopped, the operation of stirring was stopped, and then the reaction solution remaining in the esterification reactor ③ was extracted through the line 30. The extracted solution was supplied to the esterified compound purifying step (not shown) and distilled therein.

Then, 6 m³ of water was supplied through the line 40 to the esterification reactor ③ and stirred and heated under normal pressure till the boiling temperature. Consequently, water was expelled by distillation through the top of the dehydration column ⑳ equipped to the esterification reactor ③ together with n-butanol and butyl acrylate remaining in the fluidized-bed type esterification reactor ③.

The solution in the esterification reactor ③ was continuously introduced into the resin separation vessel ⑲ disposed adjacently thereto and left standing therein till the resin, i.e. a solid catalyst, was precipitated. At this time, the extraction of the cleaning fluid through the line 24 was omitted and the resin precipitated in the resin separation vessel ⑲ was circulated together with water through the line 32 to the esterification reactor ③.

Further, water was supplied to the dehydration column ⑳ equipped to the esterification reactor ③ through the top of the column ⑳ so as to retain the liquid level in the esterification reactor ③ constant. Incidentally, the water phase in the oil-water separator ⑦ contained a minute amount of n-butanol. For the purpose of recovering this n-butanol, the water phase was supplied through the line 34 to an alcohol stripper (not shown) and the n-butanol was recovered through the top of the stripper and the water was extracted as waste water through the bottom of the stripper and introduced to the top of the dehydration column ⑳.

In the oil-water separator ⑦, the liquid expelled by distillation from the dehydration column ⑳ was separated into butanol, the organic phase containing butyl acrylate, and the water phase containing butanol, and the organic phase was recovered through the line 33 to be used as a reaction raw material.

When this procedure was continued for 20 hours, the concentration of n-butanol and butyl acrylate in the cleaning fluid was found to have fallen to below 0.1 mass %. Thus, the heating and the stirring were stopped, the resin in the resin separation vessel ⑲ was circulated to the esterification reactor ③ and cooled therein, and the water was extracted therefrom. When the ion-exchange resin was subsequently extracted from the esterification reactor ③, it emitted practically no perceptible offensive odor.

What is claimed is:

1. A method for the disposal of a spent solid catalyst in an apparatus for the production of an esterified compound comprising an esterified compound reactor provided with a part packed with a solid catalyst and a distillation part, which method is characterized by washing said spent solid catalyst in said part packed with the solid catalyst with water and/or a component of the raw material for an esterified compound, and washing at a final stage with water.

2. A method according to claim 1, wherein the cleaning fluid obtained in consequence of said washing is recovered and at least part of the recovered cleaning fluid is re-used as the raw material for production in said apparatus for the production an esterified compound.

3. A method according to claim 2, wherein said apparatus for the production of an esterified compound is provided with a plurality of esterification reactors, the part packed with the spent solid catalyst is washed with water and/or the component of the raw material for the esterified compound while at least one of said reactors and the device for the production of an esterified compound connected thereto are kept in operation and the esterification reactor packed with the spent solid catalyst is suspended from operation, and at least part of the resultant cleaning fluid is stilled in said distillation part.

4. A method according to claim 1, wherein said water is the water by-produced during the process for the production of an esterified compound.

5. A method according to claim 1, wherein said component of the raw material for said esterified compound is the alcohol to be used during the process of production of an esterified compound.

6. A method according to claim 1, wherein said washing is carried out at a temperature in the range of 20–100° C.

7. A method according to claim 1, wherein said solid catalyst is an ion-exchange resin catalyst.

8. A method according to claim 1, wherein said part packed with a solid catalyst is in a fixed-bed pattern or a fluidized-bed pattern.

9. A method according to claim 1, wherein said esterified compound is the product of esterification between (meth) acrylic acid and an alcohol.

* * * * *